United States Patent [19]

Carlino

[11] Patent Number: 5,426,098
[45] Date of Patent: Jun. 20, 1995

[54] INCREASE IN HEMATOPOIETIC PROGENITOR CELLS IN PERIPHERAL BLOOD BY TRANSFORMING GROWTH FACTOR BETA

[75] Inventor: Joseph A. Carlino, San Leandro, Calif.

[73] Assignee: Celtrix Pharmaceuticals, Inc., Santa Clara, Calif.

[21] Appl. No.: 116,253

[22] Filed: Sep. 2, 1993

[51] Int. Cl.$^6$ .................... A61K 38/36; A61K 35/12
[52] U.S. Cl. ........................................ 514/12; 514/21
[58] Field of Search ................................ 514/12, 21

[56] References Cited

U.S. PATENT DOCUMENTS 4,774,322  9/1988  Seyedin et al. .................. 530/353

FOREIGN PATENT DOCUMENTS 9100103  1/1991  WIPO .

OTHER PUBLICATIONS

Massagué, "The TGF-B family of growth and differentiation factors", Cell:51, 107–145 (1987).
Chiefetz et al., "The transforming growth factor-β system, a complex pattern of cross-reactive ligands and receptors" Cell (1987) 48:409–415.
Ikeda et al., "Human transforming growth factor type β2: Production by a prostatic adenocarcinoma cell line, purification, and initial characterization" Biochemistry (1987) 26:2406–2410.
Seyedin et al., "Cartilage-inducing factor-B is a unique protein structurally and functionally related to transforming growth factor-β" J. Biol. Chem. (1987) 262(5):1946–1949.
Dernyck et al., "A new type of transforming growth factor-β, TGF-β3" EMBO J. (1988) 7(12):3737–3743.
Madisen et al., "Transforming growth factor-β2: cDNA cloning and sequence analysis" DNA (1988) 7(1):1–8.
Ignotz, "Transforming growth factor-β stimulates the expression of fibronectin and collagen and their incorporation into the extracellular matrix" J. Biol. Chem. (1986) 261(9):4337–4345.
Goey et al., "Inhibition of early murine hemopoietic progenitor cell proliferation after in vivo locoregional administration of transforming growth factor-β1" J. Immunol. (1989) 143(3):877–880.
Carlino et al., "TGF-β2 decreases chemotherapy-induced mortality in mice" J. Cell. Biochem. (1993) 178:61 (abstract No. E 105).
Carlino et al., "Transforming growth factor β1 systemically modulates granuloid, erythroid, lymphoid, and thrombocytic cells in mice" Exp. Hematol. (1992) 20:943–950.
Hestdal et al., "Increased granulopoiesis after sequential administration of transforming growth factor-β1 and granulocyte-macrophage colony-stimulating factor" Exp. Hematol. (1993) 21:799–805.
Massagué, "The TGF-β family of growth and differentiation factors" Cell (1987) 49:437–438.

(List continued on next page.)

Primary Examiner—Howard E. Schain
Assistant Examiner—P. Lynn Touzeau
Attorney, Agent, or Firm—Morrison & Foerster

[57] ABSTRACT

TGFβ is used to increase the numbers of stem cells in a subject's peripheral blood. Then the subject's blood is drawn and the stem cells removed. After myelosuppressive therapy is administered to the subject, the stem cells are administered to the subject. An alternate method provides for TGFβ administration to a donor subject whose blood is drawn and from whose blood the stem cells are removed; after a recipient subject receives myelosuppressive therapy, the stem cells are administered to the recipient subject.

5 Claims, No Drawings

OTHER PUBLICATIONS

Roberts et al., "Transforming growth factor β" *Adv. Cancer Res.* (1988) 51:107–145.

Ellingsworth et al., "Antibodies to the N-terminal portion of cartilage-inducing factor A and transforming growth factor β" *J. Biol. Chem.* (1986) 261(26):12362–12367.

Kessinger et al., "The evolving role of autologous peripheral stem cell transplantation following high-dose therapy for malignancies" *Blood* (1991) 77(2):211–213.

Kessenger et al., "High-dose therapy and autologous peripheral blood stem cell transplantation for patients with lymphoma" *Blood* (1989) 74(4):1260–1265.

Morse et al., "Peripheral blood stem cell transfusion for marrow replacement" *Annals Clin. Lab. Sci.* (1992) 22(4):221–225.

Takaue et al., "Isolation and storage of peripheral blood hematopoietic stem cells for autotransplantation into children with cancer" *Blood* (1989) 74(4):1245–1251.

Kessinger et al., "Autologous peripheral hematopoietic stem cell transplantation restores hematopoietic function following marrow ablative therapy" *Blood* (1988) 71(3):723–727.

INCREASE IN HEMATOPOIETIC PROGENITOR CELLS IN PERIPHERAL BLOOD BY TRANSFORMING GROWTH FACTOR BETA

TECHNICAL FIELD

The invention relates generally to multifunctional cytokines and their use in inducing hematopoietic progenitors. Specifically, the invention relates to the use of transforming growth factor beta to increase the number of hematopoietic progenitor cells in peripheral blood.

BACKGROUND ART

Growth factors are polypeptides which stimulate a wide variety of biological responses (e.g., DNA synthesis, cell division, cell differentiation, expression of specific genes, etc.) in a defined population of target cells. A variety of growth factors have been identified including transforming growth factor-$\beta$1 (TGF$\beta$1), TGF$\beta$2, TGF$\beta$3, epidermal growth factor (EGF), platelet-derived growth factor (PDGF), fibroblast growth factor (FGF), insulin-like growth factor-I (IGF-I), and IGF-II.

GROWTH FACTORS

The family of peptides known as TGF$\beta$ can regulate both cell growth and differentiation. These polypeptides can both stimulate and inhibit cell proliferation depending largely on the cell type and environment. TGFs of some type have been found in almost all tissues from all species of animals which have been examined so far.

TGF$\beta$2 is a well characterized growth factor. As noted above, it is a polypeptide having a molecular weight of about 25,000 Daltons and exists as dimer composed of two 12,500 Dalton subunits linked by a disulfide bond (Chiefetz et al., (1987) *Cell* 48:408–415; Ikeda et al., (1987) *Biochemistry* 26:2406–2410). TGF$\beta$ has been isolated from a variety of sources including bovine demineralized bone (Seyedin et al., (1987) *J. Biol. Chem.* 262:1946–1949), porcine platelets (Cheifetz et al., (1987) *Cell* 48:409–415), and the human prostatic adenocarcinoma cell line, PC-3. Ikeda et al., (1987) *Biochemistry* 26:2406–2410. Methods for separating and purifying TGF$\beta$2 are given in U.S. Pat. No. 4,774,322 to Seyedin et al.

TGF$\beta$1 and TGF$\beta$2 are found in many of the same cells. However, their mature sequences have only about 75–80% homology. Derynck et al., (1987) *EMBO J.* 7: 3737–3743. It has been established that the several species of TGF$\beta$ are coded for by different genes. Madisen et al., (1988) *DNA* 7: 1–8.

TGF$\beta$2 has been found to stimulate collagen glycoprotein synthesis as well as cellular proliferation and migration involved in the wound healing process. See, Ignotz, "Transforming Growth Factor-$\beta$ Stimulates the Expression of Fibronectin in Collagen and their Incorporation into the Extracellular Matrix", (1986) *J. Biol. Chem.* 261:4337–45.

The growth suppression of bone marrow hematopoietic progenitors by TGF$\beta$ has been described and postulated to be of potential use for reducing the sensitivity of these cells to the cytotoxic effects of chemotherapeutic drugs and radiation. Goey et al. (1989) *J. Immunol.* 143:877–883; Keller et al., EP patent application WO 9100103; Carlino et al. (1993) *J. Cell. Biochem.* 178:61. Furthermore, an increase in lymphoid cells in the peripheral blood of mice has been demonstrated following administration of TGF$\beta$1. Carlino et al. (1992) *Exp. Hematol.* 20:943. Finally, the sequential administration of TGF$\beta$1 and granulocyte-macrophage-colony stimulating factor (GM-CSF) to mice has been shown to increase the numbers of mature granulocytes in the peripheral blood and increase the numbers of CFU-GM in the bone marrow. Hestdal et al. (1993) *Exp. Hematol.* 21:799. None of these documents discloses the effect of TGF$\beta$ on hematopoietic progenitors in blood.

Transforming growth factor $\beta$1 (TGF$\beta$1) is a multifunctional cytokine that affects the proliferation and differentiation of a variety of cell types, including hematopoietic stem cells. Massague (1987) *Cell* 49:437; and Roberts (1988) *Adv. Cancer Res.* 51: 107. Immunohistochemical localization of TGF$\beta$1 in the bone marrow and fetal hematopoietic sites suggests that it plays a regulatory role in hematopoiesis. Ellingsworth et al. (1986) *J. Biol. Chem.* 261:12362. Therefore, studies were performed to examine the effects of TGF$\beta$ treatment on hematopoiesis in vivo in order to evaluate how exogenous TGF$\beta$ might be used to regulate these cell types.

HEMATOPOIETIC SYSTEM

Red and white blood cells are derived from an undifferentiated progenitor cell in the bone marrow called the pluripotent stem cell. A stem cell is one which is capable of both self-renewal and differentiation. Pluripotent stem cells can become lymphoid precursors, which then produce the lymphocytes that constitute the immune system. Stem cells can also give rise to the precursors of erythrocytes (red blood cells), platelets, granulocytes, and monocytes. The control of stem cell proliferation and differentiation into mature, peripheral cells is poorly understood. For the most part stem cells and progenitor cells remain in the bone marrow and are extremely rare in peripheral blood.

Hence, administering stem cells or progenitor cells to patients whose own primitive cells have been destroyed by chemotherapy or radiation has required bone marrow transplantation. A method for increasing the numbers of stem cells and/or progenitor cells in the peripheral blood could help avoid painful bone marrow transplants and aid in autologous transfusions.

A progenitor and/or stem cell can be identified in bone marrow and peripheral blood of certain laboratory animals as a colony-forming unit-spleen (CFU-S). CFU-S are measured in mice by the appearance of macroscopic colony in the spleens. Each colony represents a stem cell or primitive progenitor of the granuloid, erythroid, monocyte, or megakaryocyte lineages. Other progenitor cell types such as colony-forming units-granulocytes/macrophages (CFU-GM) are somewhat more mature cell types and are capable of differentiating only into cells of the granuloid and monocyte lineages. Various studies involving the treatment of uniform and mixed cell populations with purified growth factors provide information about the mechanism underlying the differentiation and maturation of hematopoietic cells as well as insight into various disorders of hematopoiesis.

CURRENT CANCER THERAPIES

The objective of cancer treatment is to kill cancer cells without killing the host. In radiation therapy, cells are killed by exposure to ionizing radiation. In chemotherapy, cells are killed by chemical poisons. The suppressive effects of chemical and radiation therapies on hematological parameters have been discussed in *Principles of Cancer Treatment*, Ed. by Carter, Glatstein, Livingston; McGraw-Hill, New York, 1982.

Cytopenias are conditions of deficiencies in the cellular elements of the blood. Cytopenias like anemia and thrombocytopenia frequently develop during the course of chemotherapy or radiation therapy and result in an increased risk of bleeding and other disorders. Patients who receive systemic chemotherapy may also develop leukopenia or granulocytopenia (white cell depletion) and increased risk of infection.

Traditional therapies for such conditions include platelet transfusions or red blood cell transfusions. Other therapies include attempts at stimulating the bone marrow to produce more leukocytes; however, these therapies are not consistently successful.

This patent application provides an invention for reducing the adverse side effects of chemo- and radiation therapy by the administration of TGF$\beta$. TGF$\beta$ increases the number of pluripotent stem cells in the peripheral circulation which then can proliferate and mature into various blood cell types. These peripheral stem or progenitor cells can then compensate for the loss due to chemotherapy or radiation therapy.

DISCLOSURE OF INVENTION

One embodiment of the present invention provides a method for increasing the number of circulating stem cells in the peripheral blood of a subject by the administration of TGF$\beta$.

In yet another embodiment, there is provided a method for facilitating hematopoietic recovery in a subject. This method comprises administering a pharmaceutically effective dose of TGF$\beta$ to the subject prior to or after myelosuppressive therapy.

In another embodiment, there is provided a method for inducing hematopoietic recovery in a subject treated with myelosuppressive therapy. Before the subject undergoes myelosuppressive therapy, this method comprises the steps of administering a pharmaceutically effective dose of TGF$\beta$ to the subject. Then the subject's peripheral blood is drawn, and the progenitor cells are removed from the drawn blood. After the myelosuppressive therapy is administered, the progenitor cells are returned to the subject.

In another embodiment, a donor subject receives TGF$\beta$ and donates peripheral blood from which the progenitor cells are removed. Then the donor subject's progenitor cells are administered to the recipient subject who has received myelosuppressive therapy.

MODES FOR CARRYING OUT THE INVENTION

A. Definitions

It must be noted that as used in this specification and the appended claims, the singular forms "a", "an" and "the" include plural referents unless the context clearly dictates otherwise.

The term "TGF$\beta$" or transforming growth factor $\beta$ refers to the proteins TGF$\beta$1 and TGF$\beta$2, and related proteins which are capable of binding to TGF$\beta$ receptors and effecting TGF$\beta$ type activity. TGF$\beta$ includes all TGF$\beta$-like proteins, whereas the terms TGF$\beta$1 and TGF$\beta$2 indicate only those specific proteins as described in U.S. Pat. No. 5,104,977 (U.S. Dept. of Commerce) and U.S. Pat. No. 4,774,322 (Celtrix Pharmaceuticals, Inc.), respectively, and hereby incorporated by reference.

"Mammals" are defined as humans and mammalian farm and sport animals and pets. Farm animals include, but are not limited to, cows, hogs, and sheep. Sport animals include, but are not limited to, dogs and horses. The category pets includes, but is not limited to, cats, dogs, and hamsters.

The method of the present invention contemplates treating a subject to increase hematopoietic stem cells in the peripheral with TGF$\beta$. The term "subject" as used herein refers to a living vertebrate animal such as a mammal or bird in need of treatment, i.e., the subject suffers from a suppressed hematopoietic system.

"Stem cells" include pluripotent stem cells which are capable of self-renewal and differentiation. Stem cells can give rise to the precursors of erythrocytes, platelets, granulocytes and monocytes. Included in this definition of stem cells are peripheral blood fractions from which most of the differentiated cells have been removed. Most of these stem cell fractions include some early, apparently undifferentiated progenitors of at least erythrocytes, platelets, granulocytes and monocytes. Such early progenitor cells also are included in this definition of stem cells.

The term "treatment" as used herein shall mean providing a subject with an amount of TGF$\beta$ sufficient to increase the numbers of stem cells in the peripheral blood.

B. General methods

Both the purification of progenitors from the peripheral blood, and the benefits of re-infusion of autologous or syngeneic progenitors following myelosuppressive therapy have been described in the literature. Morse et al. (1992) *Ann. Clin. Lab. Sci.* 22:221-25; Kessinger and Armitage (1991) *Blood* 77:211-13; Kessinger et al. (1988) *Blood* 171:723-27; Kessinger et al. (1989) *Blood* 74:1260-65; Takam et al. (1989) *Blood* 74:1245-51.

The use of classic colony stimulating factors (eg GM-CSF) has also been described to induce a myelopoietic response, resulting in an increase in peripheral blood progenitor cells. The present invention describes the unexpected use of TGF$\beta$1 and TGF$\beta$2 to increase peripheral progenitor cells. These peripheral progenitor cells could then be stored or expanded for later re-infusion into the patient following myelosuppressive therapy, e.g., chemotherapy or radiation.

TGF$\beta$ can also be given to stem cell donors whose HLA transplantation antigens match those of the patient about to undergo myelosuppressive therapy. TGF$\beta$ can increase the numbers of progenitor cells in the peripheral blood. Once that occurs, the donor's blood is drawn and the stem cells are separated from the blood by means well known in the art. These methods involve, for example, the use of monoclonal antibodies which bind to stem cells and/or progenitor cells and separate them from other peripheral blood cells. One such separation method is the Celprate LC ® cell separation method (Cell-Pro, Bothell, Wash.). The separated cells may then be given to the patient who has undergone myelosuppressive therapy. If desired, the progenitor cells can be expanded (caused to multiply) by means known in the art prior to administration.

Although a considerable amount of literature exists about the effects of TGF$\beta$ on hematopoietic stem cells, its physiological role in hematopoiesis is not fully understood.

In accordance with the method of the present invention, TGF$\beta$ is a protein obtained from natural or recombinant sources. Most preferably, TGF$\beta$ is human and is made by recombinant means and designated rhTGFβ. Pharmaceutical formulations of the invention include TGFβ with a pharmaceutically acceptable excipient. Suitable excipients include most carriers approved for parenteral administration, including water, saline, Ringer's solution, Hank's solution, and solutions of glucose, lactose, dextrose, ethanol, glycerol, albumin, plasma, other protein-containing solutions and the like. These compositions may optionally include stabilizers, antioxidants, antimicrobials, preservatives, buffering agents, surfactants, and other accessory additives. The TGFβ may also be delivered in a slow release form from a suitable carrier.

Various vehicles may be used with the present invention. A thorough discussion of suitable vehicles for parenteral administration may be found in E. W. Martin, "Remington's Pharmaceutical Sciences" (Mack Pub. Co., current edition). Sections relating to the excipient vehicles and formulating are incorporated herein by reference. Such formulations are generally known to those skilled in the art and are administered systemically to provide systemic treatment.

The precise dosage necessary will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation with animal models, as described below. In general terms, an effective dose of TGFβ for systemic treatment will range from about 0.1 μg/kg to about 10 mg/kg of body weight.

The methods and compositions of the invention are useful for treating prior to myelosuppressive therapies, e.g. chemotherapy or radiation.

In accordance with one method of use, the TGFβ may be administered systemically. For systemic delivery, the oral, intranasal, rectal and/or parenteral routes can be utilized. Parenteral routes include but are not limited to subcutaneous, intraperitoneal, intramuscular and intravenous injection or other conventional routes of administration. Additionally, TGFβ may be delivered in a slow release form from a suitable carrier. Preferably, the protein is injected subcutaneously, intramuscularly, most preferably, the protein is administered by intravenous injection. TGFβ appears not to be toxic at the injection site.

In accordance with another method of use, the TGFβ may be administered locally to sites of hematopoiesis, including, but not limited to, bone marrow, thymus, spleen, liver or kidney.

C. Examples

The following examples are put forth so as to provide those of ordinary skill in the art with a complete disclosure and description of how to extract, isolate, formulate and use the compositions and methods of the invention and are not intended to limit the scope of what the inventors regard as their invention. Efforts have been made to insure accuracy with respect to numbers used (e.g., amounts, times, temperature, etc.), but some experimental error and deviations should be accounted for. Unless indicated otherwise, parts are parts by weight, temperature is in degrees centigrade, pressure is at or near atmospheric, and other parameters are conventional and in accordance with those normally accepted by those skilled in the art.

EXAMPLE 1

In the present study, a mouse model was used to show the effects of TGFβ1 on the numbers of peripheral blood stem cells which can be used to reconstitute a functioning hematopoietic system. The injection of stem cells into the irradiated mouse provides a model for the human condition in which peripheral blood stem cells can be implanted following immunosuppressive therapy.

Male C3H/He mice (Charles River Laboratories, Wilmington, Mass.), aged 6–8 weeks and weighing approximately 25 grams, were maintained on standard mouse chow and water ad libitum. Mice received 14 daily subcutaneous (s.c.) injections (0.2 ml) at the base of the tail of 25 micrograms of bovine bone derived TGFβ1 (1 mg/kg) in phosphate-buffered saline (PBS) containing 0.1% mouse serum albumin (MSA; Sigma Chemical Company, St. Louis, Mo.). Control mice received sham injections of MSA/PBS.

The effects of TGFβ1 on the numbers of myeloid stem cells, spleen colony-forming units (CFU-S), in the peripheral blood and bone marrow were investigated. One day after the final injection, terminal blood samples were obtained from anesthetized mice by cardiac puncture and anticoagulated with ethylenediaminetetraacetic acid (EDTA). Single-cell suspensions from bone marrow (femur) were prepared in Iscove's Minimum essential medium (IMEM; GIBCO, Grand Island, N.Y.).

Bone marrow ($5 \times 10^4$ cells) and peripheral white blood cells ($10^6$ cells) from these mice (4–5 mice per group) were injected intravenously (IV) into irradiated syngeneic recipients which were immunosuppressed. Fourteen days after the cell injections, the recipient spleens were explanted and examined under a dissecting microscope. The number of colonies observed in an explanted spleen represented the number of CFU-S transferred into the recipient per $10^5$ cells. The results are shown in Table 1.

Levels of CFU-S in the bone marrow of TGFβ1 treated mice one day following treatment were similar to those in vehicle-treated mice. In contrast, significantly elevated levels of CFU-S were present in the peripheral blood of TGFβ1 treated mice. A fourteen-fold increase was seen in the number of CFU-S from the peripheral blood of mice treated with TGFβ1, as compared to mice treated with vehicle alone.

The CFU-S represent cells capable of restoring the hematopoietic system following myelosuppressive treatment. The increase in CFU-S from the peripheral blood of TGFβ1-treated mice indicates that TGFβ1 increased the frequency of stem cells per $10^5$ cells. This result indicates that TGFβ1-induced, peripheral blood stem cells can survive and colonize a myelosuppressed animal.

TABLE 1

| Donor cells | CFU-S/$10^5$ Cells[a] | Colony Content | | | | |
|---|---|---|---|---|---|---|
| | | E | G | Mix | M | Total |
| Bone Marrow | | | | | | |
| Vehicle | 13.45 ± 2.86 | 39 | 9 | 7 | 3 | 58 |
| TGFβ1 | 9.50 ± 2.70 | 47 | 5 | 1 | 3 | 56 |
| Peripheral Blood | | | | | | |
| Vehicle | 0.189 ± 0.08 | 4 | 0 | 0 | 0 | 4 |

TABLE 1-continued

| Donor cells | CFU-S/$10^5$ Cells[a] | Colony Content | | | | |
|---|---|---|---|---|---|---|
| | | E | G | Mix | M | Total |
| TGFβ1 | 2.26 ± 0.15[b] | 56 | 3 | 40 | 1 | 100 |

[a]Mean ± SEM of 8–12 mice per group
[b]Significantly different from vehicle value at p<.01 by Dunnett's t test.
E = erythroid, G = granulocytic, Mix = mixed, M = megakaryocytic

EXAMPLE 2

In the present study, a mouse model was used to show the effect of TGFβ2 on the numbers of peripheral blood stem cells which can be used to reconstitute a functioning hematopoietic system.

Male Balb/c mice aged 6–8 weeks weighing approximately 25 grams were maintained on standard mouse chow and water ad libitum. Two groups of mice (five mice per group) were given daily IV injections of either placebo or 1 μg (40 μg/kg) of rTGFβ2 for seven days. The effects of rTGFβ2 on the numbers of granulocyte-macrophage precursors in the peripheral blood were investigated.

Blood samples were collected from the mice one day after the final treatment. White blood cells (WBC) were isolated from individual animal samples and were the pooled within groups. The pooled samples were then put into a standard 7-day CFU-GM colony assay, according to the protocol found in the Moore et al. chapter on Measurement of Interleukin-3 and Other Hematopoietic Growth Factors, in: *Current Protocols in Immunology. Vol.* 1. Ed., by Coligan et al. (Wiley & Sons, New York, 1991). The number of granulocyte-macrophage precursors (CFU-GM) per $2 \times 10^6$ WBC was then determined.

The results, as shown in Table 2, show a five-fold increase in the number of CFU-GM per $2 \times 10^6$ WBC in the rTGFβ2-treated mice, as compared to vehicle-controlled mice, with a concomitant increase in CFU-GM per ml of whole blood.

The CFU-GM represent cells capable of restoring the granuloid and macrophage lineages. The increase in CFU-GM from the peripheral blood of TGFβ2-treated mice indicates that TGFβ2 increased the frequency of GM progenitor cells per $10^6$ cells. These results indicate that TGFβ2 increases the number of peripheral GM precursor cells which are capable of generating the granuloid and macrophage lineages.

TABLE 2

| | Vehicle Control | TGFβ2 |
|---|---|---|
| A) WBC per ml $\times 10^6$ | 2.65 (pooled average) | 3.55 |
| B) CFU-GM per $2 \times 10^6$ WBC | 7 ± 1 (mean of triplicate of pooled samples) | 36 ± 7 |
| C) CFU-GM per ml whole blood (A × B) | 9.3 | 63.9 |

I claim:

1. A method for increasing the numbers of circulating stem cells in a subject, comprising systemically administering a pharmaceutically effective dose in the range from about 0.1 μg/kg to about 10 mg/kg of TGFβ-2 to the subject prior to the subject receiving myelosuppressive therapy.

2. A method for increasing the numbers of circulating stem cells in a subject, comprising systemically administering a pharmaceutically effective dose in the range from about 0.1 μg/kg to about 10 mg/kg of TGFBβ-2 to the subject after the subject receives myelosuppreesive therapy.

3. A method for increasing the numbers of circulating stem cells in a subject treated with myelosuppressive therapy, comprising the steps of:
   a) prior to myelosuppressive therapy, systemically administering a pharmaceutically effective dose in the range from about 0.1 μg/kg to about 10 mg/kg of TGFβ-2 to the subject;
   b) drawing peripheral blood from the subject;
   c) removing stem cells from the subject's blood; and
   d) after the myelosuppressive therapy is administered, administering the stem cells to the subject.

4. A method for increasing the numbers of circulating stem cells in a recipient subject treated with myelosuppreseive therapy, comprising the steps of
   a) systemically administering a pharmaceutically effective dose in the range from about 0.1 μg/kg to about 10 mg/kg of TGFβ-2 to a donor subject;
   b) drawing peripheral blood from the donor subject;
   c) removing stem cells from the donor subject's blood; and
   d) after the myelosuppressive therapy is administered, administering the stem cells to the recipient subject.

5. The method of claim 4 wherein the donor subject and the recipient subject are HLA matched.

* * * * *